(12) United States Patent
Garcia Molina et al.

(10) Patent No.: US 11,779,267 B2
(45) Date of Patent: Oct. 10, 2023

(54) MACRO/MICRO-STRUCTURE OF SLEEP AND SIMILAR STATES OF CONSCIOUSNESS TO OPTIMIZE PAIN TREATMENT

(71) Applicant: KONINKLIJKE PHILIPS N.V., Eindhoven (NL)

(72) Inventors: Gary Nelson Garcia Molina, Madison, WI (US); Gaurav Trivedi, Pittsburgh, PA (US); Gino Iasella, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 137 days.

(21) Appl. No.: 17/106,883

(22) Filed: Nov. 30, 2020

(65) Prior Publication Data
US 2021/0282704 A1    Sep. 16, 2021

Related U.S. Application Data

(60) Provisional application No. 62/990,110, filed on Mar. 16, 2020.

(51) Int. Cl.
*A61B 5/00* (2006.01)
*A61B 5/0205* (2006.01)
(Continued)

(52) U.S. Cl.
CPC .......... *A61B 5/4818* (2013.01); *A61B 5/0205* (2013.01); *A61B 5/02405* (2013.01);
(Continued)

(58) Field of Classification Search
CPC .... A61B 2560/0223; A61B 2560/0252; A61B 2560/0257; A61B 5/0004; A61B 5/0205;
(Continued)

(56) References Cited

U.S. PATENT DOCUMENTS

| | | | |
|---|---|---|---|
| 7,801,619 B2 | 9/2010 | Gerber et al. | |
| 8,088,057 B2 | 1/2012 | Honeycutt | |

(Continued)

FOREIGN PATENT DOCUMENTS

| | | |
|---|---|---|
| WO | 02056877 A1 | 7/2002 |
| WO | 2003053426 A1 | 7/2003 |
| WO | 2004064832 A2 | 8/2004 |

OTHER PUBLICATIONS

Marca et al. "Pain and the Alpha-Sleep Anomaly: A Mechanism of Sleep Disruption in Facioscapulohumeral Muscular Dystrophy", Pain Medicine 2013;14: 487-497 (Year: 2013).*

(Continued)

*Primary Examiner* — Jonathan T Kuo
*Assistant Examiner* — Vynn V Huh (57) ABSTRACT

An apparatus and method for employing the macro- and micro-structure of sleep and similar states of consciousness to optimize pain-treatment are disclosed wherein an objective biomarker of pain-related sleep disturbance guides pain treatment from a sleep perspective. Furthermore, this concept can be extended to states of reduced consciousness such as coma or sedation. Additionally, it could be applied on individuals who are non-communicative due to injury, disease, language issues and/or infancy.

10 Claims, 5 Drawing Sheets

---

100

110 — DETECT A NUMBER OF SLEEP ARCHITECTURE SIGNAL FROM A NUMBER OF MONITORING DEVICES

120 — DETERMINE AN INDEX OF PAIN BASED AT LEAST IN PART UPON THE NUMBER OF SIGNALS

130 — GENERATE AN OUTPUT REPRESENTATIVE OF THE INDEX OF PAIN AND/OR AN ADAPTATION OF A PAIN TREATMENT IN AN INDIVIDUAL (51) Int. Cl.

| | |
|---|---|
| A61B 5/024 | (2006.01) |
| A61B 5/08 | (2006.01) |
| A61B 5/11 | (2006.01) |
| A61B 5/316 | (2021.01) |
| A61B 5/318 | (2021.01) |
| A61B 5/369 | (2021.01) |
| A61B 5/372 | (2021.01) |
| A61B 5/383 | (2021.01) |
| A61B 5/389 | (2021.01) |
| A61B 5/398 | (2021.01) |
| G16H 20/30 | (2018.01) |
| G16H 10/20 | (2018.01) |
| G16H 20/10 | (2018.01) |
| G16H 40/63 | (2018.01) |
| G16H 40/67 | (2018.01) |
| G01P 13/00 | (2006.01) |
| G16H 50/70 | (2018.01) |
| G16H 50/20 | (2018.01) |
| G16H 50/30 | (2018.01) |
| G09B 19/00 | (2006.01) |
| A61B 5/1455 | (2006.01) |
| A61B 5/38 | (2021.01) |
| A61B 5/378 | (2021.01) |

(52) U.S. Cl.
CPC ............ *A61B 5/02416* (2013.01); *A61B 5/08* (2013.01); *A61B 5/1102* (2013.01); *A61B 5/1118* (2013.01); *A61B 5/316* (2021.01); *A61B 5/318* (2021.01); *A61B 5/369* (2021.01); *A61B 5/372* (2021.01); *A61B 5/383* (2021.01); *A61B 5/389* (2021.01); *A61B 5/398* (2021.01); *A61B 5/4088* (2013.01); *A61B 5/4809* (2013.01); *A61B 5/4812* (2013.01); *A61B 5/4815* (2013.01); *A61B 5/4836* (2013.01); *A61B 5/6801* (2013.01); *A61B 5/6892* (2013.01); *A61B 5/6898* (2013.01); *A61B 5/7246* (2013.01); *A61B 5/7264* (2013.01); *A61B 5/7267* (2013.01); *A61B 5/7278* (2013.01); *G01P 13/00* (2013.01); *G16H 10/20* (2018.01); *G16H 20/10* (2018.01); *G16H 20/30* (2018.01); *G16H 40/63* (2018.01); *G16H 40/67* (2018.01); *G16H 50/20* (2018.01); *G16H 50/30* (2018.01); *G16H 50/70* (2018.01); *A61B 5/024* (2013.01); *A61B 5/02438* (2013.01); *A61B 5/0816* (2013.01); *A61B 5/1103* (2013.01); *A61B 5/1123* (2013.01); *A61B 5/14552* (2013.01); *A61B 5/378* (2021.01); *A61B 5/38* (2021.01); *A61B 5/6802* (2013.01); *A61B 5/6891* (2013.01); *G09B 19/00* (2013.01)

(58) Field of Classification Search
CPC . A61B 5/02116; A61B 5/024; A61B 5/02405; A61B 5/02416; A61B 5/02438; A61B 5/08; A61B 5/0816; A61B 5/0873; A61B 5/1102; A61B 5/1103; A61B 5/1118; A61B 5/1123; A61B 5/14552; A61B 5/316; A61B 5/318; A61B 5/369; A61B 5/372; A61B 5/374; A61B 5/377; A61B 5/378; A61B 5/38; A61B 5/383; A61B 5/389; A61B 5/398; A61B 5/4088; A61B 5/4809; A61B 5/4812; A61B 5/4815; A61B 5/4818; A61B 5/4836; A61B 5/6801; A61B 5/6802; A61B 5/681; A61B 5/6891; A61B 5/6892; A61B 5/6898; A61B 5/7246; A61B 5/7257; A61B 5/7264; A61B 5/7267; A61B 5/7275; A61B 5/7278; G01P 13/00; G09B 19/00; G16H 10/20; G16H 20/10; G16H 20/30; G16H 20/70; G16H 40/63; G16H 40/67; G16H 50/20; G16H 50/30; G16H 50/70
USPC ........................ 600/26, 544, 545; 700/91–93
See application file for complete search history.

(56) References Cited

U.S. PATENT DOCUMENTS

| | | | |
|---|---|---|---|
| 10,232,115 B2 | 3/2019 | Osorio | |
| 10,279,179 B2 | 5/2019 | Gozani et al. | |
| 2014/0276549 A1* | 9/2014 | Osorio | A61B 5/165 |
| | | | 604/503 |
| 2016/0250470 A1 | 9/2016 | Malackowski | |
| 2018/0229040 A1* | 8/2018 | Srivastava | A61B 5/4836 |

OTHER PUBLICATIONS

International Search Report and Written Opinion, International Application No. PCT/EP2021/055833, dated Jun. 25, 2021.
Otto, K., "EEG power spectrum analysis for monitoring depth of anaesthesia during experimental surgery", Laboratory Animals, 2008.
G. Lavigne, M. T. Smith, R. Denis, and M. Zucconi, "Pain and Sleep," in Principles and Practice of Sleep Medicine, 2011, pp. 1442-1451.
M. Jiang, R. Mieronkoski, A. Rahmani, N. Hagelberg, S. Salantera, and P. Liljeberg, "Ultra-Short-Term Analysis of Heart Rate Variability for Real-time Acute Pain Monitoring with Wearable Electronics," in 2017 IEEE International Conference on Bioinformatics and Biomedicine (BIBM) Ultra-Short-Term, 2017, pp. 1025-1032.
F. Shaffer and J. P. Ginsberg, "An Overview of Heart Rate Variability Metrics and Norms," Front. Public Heal., vol. 5, No. September, pp. 1-17, 2017.
R. M. Wittig, F. J. Zorick, D. Blumer, M. Heilbronn, and T. Roth, "Disturbed sleep in patients complaining of chronic pain," J.Nerv. Ment.Dis., vol. 170, No. 7. pp. 429-431, 1982.
G. Garcia-molina et al., "Hybrid in-phase and continuous auditory stimulation significantly enhances slow wave activity during sleep," in 2019 41st Annual International Conference of the IEEE Engineering in Medicine and Biology Society (EMBC), 2019, pp. 4052-4055.
G. Garcia-Molina et al., "Closed-loop system to enhance slow-wave activity," J. Neural Eng., vol. 15, No. 6, pp. 1-11, 2018.
E. Bresch, U. Grossekathofer, and G. Garcia-Molina, "Recurrent deep neural networks for real-time sleep stage classification from single channel EEG," Front. Comput. Neurosci., vol. 12, No. 2018, pp. 1-12, 2018.
P. Fonseca et al., "Validation of Photoplethysmography-Based Sleep Staging Compared With Polysomnography in Healthy Middle Aged Adults," Sleep, vol. 3, 2017.
R. D. Sanders, G. Tononi, S. Laureys, and J. W. Sleigh, "Unresponsiveness versus unconsciousness," Anesthesiology, vol. 116, No. 4, pp. 946-959, Nov. 2012.

* cited by examiner

MACRO/MICRO-STRUCTURE OF SLEEP AND SIMILAR STATES OF CONSCIOUSNESS TO OPTIMIZE PAIN TREATMENT

CROSS-REFERENCE TO PRIOR APPLICATIONS

This application claims the benefit of U.S. Provisional Application No. 62/990,110, filed on 16 Mar. 2020. This application is hereby incorporated by reference herein.

BACKGROUND OF THE INVENTION

1. Field of the Invention

The present invention pertains to the optimization of pain treatment, and, in particular, to an apparatus and method for employing the macro- and/or micro-structure of sleep (and similar states of consciousness) to optimize pain-treatment.

2. Description of the Related Art

Chronic pain is reported by approximately one out of four adults in the general population, and two thirds of them complain of poor sleep quality. In many patients, the relationship between pain and poor sleep can transform into a vicious-cycle where poor sleep exacerbates pain and vice versa.

The impact of acute pain on sleep (e.g. delay in sleep onset, sleep awakening, poor sleep quality, low restorative effectiveness) is usually short term and reversible. However, the presence of chronic pain can be associated with a vicious-cycle pattern, i.e. a day with intense pain followed by a night of poor sleep quality, and a night of poor sleep increasing the reports of pain on the next day. Chronic pain is reported by approximately one out of four adults in the general population, and two thirds of them complain of poor sleep quality. G. Lavigne, M. T. Smith, R. Denis, and M. Zucconi; "Pain and Sleep" in "Principles and Practice of Sleep Medicine" 2011, pp. 1442-51.

The pharma and neuro-stimulation industries have considered the issue of pain during sleep. Pain-related sleep disturbances are considered as an aspect that can be resolved if the underlying pain is treated (U.S. Pat. No. 8,088,057; EP 1,363,608), successful pain treatment can be determined if sleep is improved (U.S. Pat. No. 7,801,619), and sleep/wake detection determines the type of pain treatment (U.S. Pat. No. 10,279,179). It has been known to treat fybromyalgia (1% prevalence) which notoriously affects sleep (WO 2003053426), and it has additionally been known to treat joint pain and improve sleep with estrogen agonist/antagonist (EP 1,599,199).

Nevertheless, improvements in the evaluation of pain-related sleep disturbances would be desirable.

SUMMARY OF THE INVENTION

Accordingly, it is an object of the present invention to provide an improved apparatus and method for employing the macro- and micro-structure of sleep and/or similar states of consciousness to optimize pain-treatment that overcomes the shortcomings of conventional systems and methods for providing pain treatment. This object is achieved according to one embodiment of the present invention by providing an apparatus and method wherein an objective biomarker of pain-related sleep disturbance guides pain treatment from a sleep perspective. Furthermore, this concept can be extended to states of reduced consciousness such as coma or sedation. Additionally, it could be applied on individuals who are non-communicative due to injury, disease, language issues and/or infancy.

Current clinical approaches for pain management, consider sleep complaints as secondary issues that will likely resolve once pain is treated. However, insufficient attention is given to profound alterations (sometimes unbeknownst to the patient) caused by pain on sleep architecture and the micro-structure of sleep, and how an evaluation of these alterations might provide guidance related to treatment plans.

Notwithstanding the profound and potentially long-lasting impact that pain can have on sleep, the pharma and neuro-stimulation industries on pain treatment have not considered sleep-specific aspects adversely impacted by pain. The impact of pain spans beyond the subjective sleep quality and affects sleep architecture, typically by fragmenting Non-Rapid Eye Movement (NREM) and Rapid Eye Movement (REM) sleep, the micro-structure of sleep, by injecting arousal-like patterns of activity into sleep (primarily deep NREM sleep), and autonomic activity during sleep (by decreasing heart-rate variability during deep sleep). The disclosed and claimed concept advantageously comprehensively considers the adverse impact of pain on sleep to build an index of pain-related sleep disturbances at the macroscopic and microscopic levels. This index is then utilized to quantify the effect of pain treatment on sleep and to track the treatment effectiveness on sleep specific complaints. This index can also be used to modify pain treatment and to track the efficacy of the modified pain treatment in order to optimize pain treatment.

The disclosed and claimed concept advantageously utilizes a combination of pain indicators in a number of signals such as: 1) a sleep electroencephalogram (EEG) (the degree of alpha intrusion in deep-sleep), 2) a sleep cardiac signal or cardiac input (electrocardiogram (ECG or EKG) or photoplethysmogram (PPG)), and 3) the sleep architecture (slow-wave sleep fragmentation) to build an index that reflects the effect of pain on sleep. As employed herein, the expression "a number of" and variations thereof shall refer broadly to any non-zero quantity, including a quantity of one. Alpha waves typically are in the 8-12 Hz or higher frequency band. Delta waves are typically in the 0.5-4 Hz or lower frequency band. This index plays at least two major roles: 1) it optimizes pain-treatment dosage to support sleep, and 2) it quantifies and tracks the effect of pain-treatment on sleep. Pain treatment can be based on pharmacological intervention, physical therapies, occupational therapies, sleep hygiene issues, neuro-stimulation, etc.

Accordingly, aspects of the disclosed and claimed concept are provided by an improved method of optimization of a pain treatment in an individual, the nature of which can be generally stated as including, during at least a portion a period of reduced consciousness of the individual, detecting a number of signals from a number of monitoring devices applied to the individual, determining an index of pain in the individual based at least in part upon the number of signals, and generating an output that is representative at least in part of at least one of the index of pain and an adaptation of a pain treatment of the individual.

Other aspects of the disclosed and claimed concept are provided by an improved apparatus structured to optimize a pain treatment in an individual, the nature of which can be generally stated as including a processor apparatus that can be generally stated as including a processor and a storage, an input apparatus structured to provide a number of input signals to the processor apparatus, an output apparatus structured to receive a number of output signals from the processor apparatus, and the storage having stored therein a number of instructions which, when executed on the processor, cause the apparatus to perform a number of operations, the nature of which can be generally stated as including, during at least a portion a period of reduced consciousness of the individual, detecting a number of signals from a number of monitoring devices applied to the individual, determining an index of pain (Ip) in the individual based at least in part upon the number of signals, and generating an output that is representative at least in part of at least one of the index of pain and an adaptation of a pain treatment of the individual. These optionally can be real-time to influence in a closed loop the titration of medications, and/or can involve offline processing and reporting to clinicians who adjust treatment protocols such as medications, physical therapies, occupational therapies, sleep hygiene issues, neuro-stimulation, etc.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
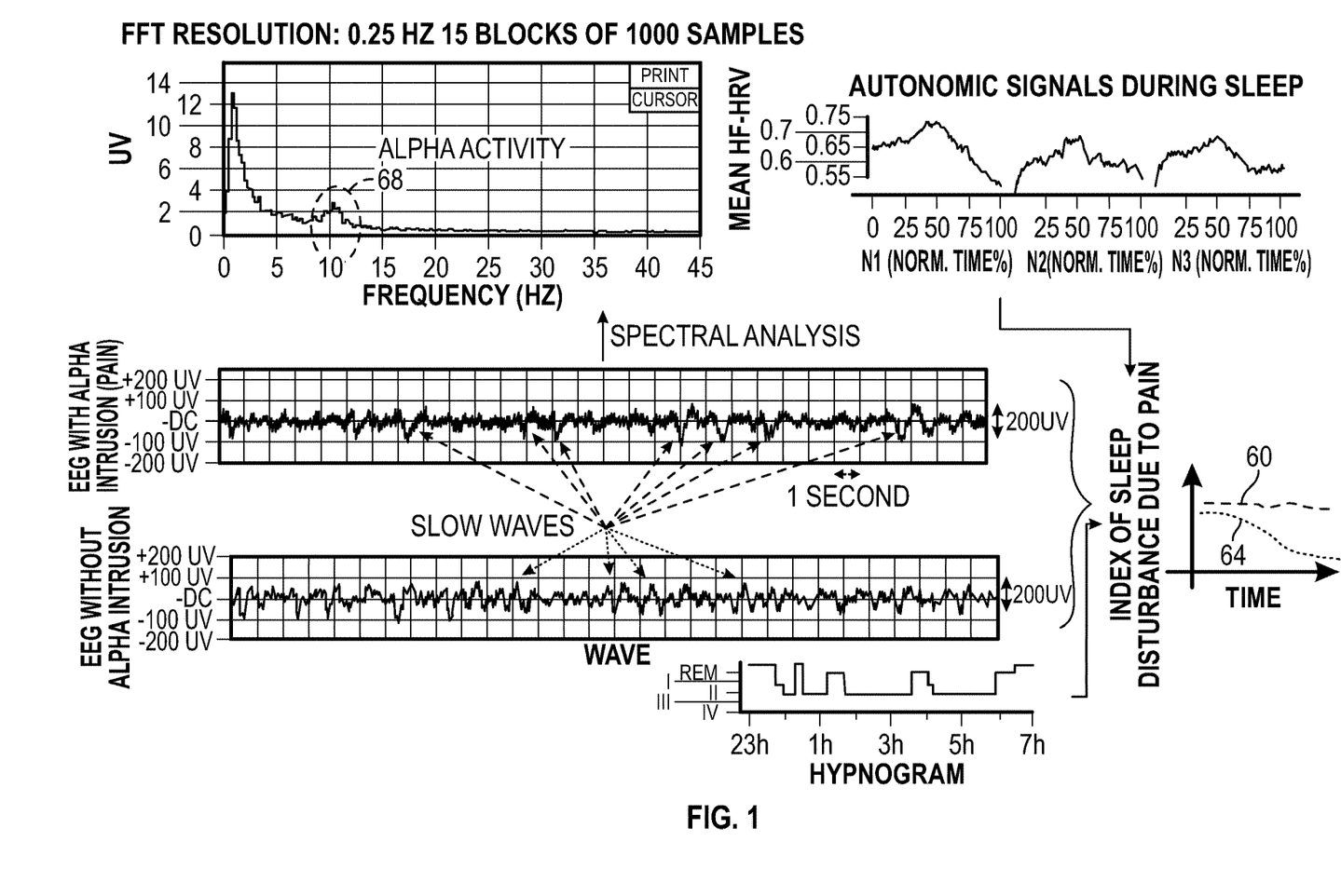
FIG. 1 is a schematic depiction of an index of sleep disturbance to detect pain-related sleep disturbance and to track treatment effectiveness in accordance with an aspect of the disclosed and claimed concept.

FIG. 1 illustrates the essential block diagram of this invention. From a sleep period which can be of any arbitrary duration but ideally includes a full sleep cycle, two types of information are extracted: 1) sleep micro-structure using physiology signals (e.g. EEG, PPG), and 2) sleep macro-structure which, in the disclosed and claimed concept, includes a hypnogram. The index "Ip" of sleep disturbance, which is described in greater detail elsewhere herein, and which is also referred to herein as an index of pain, utilizes both information sources, i.e., micro-structure and macro-structure. As described elsewhere herein, however, Ip can also be determined using either of the two information sources, i.e., micro-structure and macro-structure, taken alone.

The sleep micro-structure considered in the context of the disclosed and claimed concept relies on the EEG and/or cardiac signals (i.e., from PPG or ECG). In other embodiments, however, sleep micro-structure values can be gained from an Electromyogram (EMG) device and technique, such as with the use of an electrode on the chin or elsewhere, or through the use of an Electrooculogram (EOG) device and technique, which detects movement of the eyes, or with the use of other detection mechanisms and techniques. All of these monitoring devices provide sleep architecture information. In the disclosed and claimed concept, therefore, sleep micro-structure can be determined from any one or more of a variety of monitoring devices, which can include EEG, PPG, ECG, EMG, and EOG, by way of example, and other detection devices which provide sleep architecture information.

Pain manifests in the EEG as high frequency oscillations (e.g. alpha waves; 8-12 Hz) in deep slow-wave sleep, as is shown in FIG. 1. In normal circumstances, such as in the absence of pain, the spectral EEG content during slow-wave sleep has very strong low-frequency (<4 Hz) dominance. Thus, the presence of alpha oscillations during slow-wave sleep is a clear anomaly that is detected with automatic methods, as in FIG. 1. For instance, a sinusoidal 1-Hz 50-microvolt peak-to-peak component in an EEG signal could be said to be indicative of deep sleep. By way of further example, a 10-Hz 20-microvolt peak-to-peak sinusoidal component in the EEG signal could be said to be indicative of an alpha intrusion, as is shown at the numeral 68 in FIG. 1, on the deep sleep, which would likewise be indicative of a pain condition during the deep sleep.

Properties of cardiac signals (ECG, PPG) such as Heart Rate Variability (HRV) and heart rate (HR) reflect pain. That is, a reduced HRV reflects pain. Furthermore, it is noted that a higher HR itself reflects pain. However, the time window over which HRV metrics need to be calculated to detect pain needs to be shorter (i.e., 30 seconds, by way of example) compared to the conventional minute-long analysis window.

M. Jiang, R. Mieronkoski, A. Rahmani, N. Hagelberg, S. Salantera, and P. Liljeberg, "Ultra-Short-Term Analysis of Heart Rate Variability for Real-time Acute Pain Monitoring with Wearable Electronics" in "2017 IEEE International Conference on Bioinformatics and Biomedicine (BIBM) Ultra-Short-Term" 2017, pp. 1025-32. At the macroscopic level pain influences sleep. Id.

These indices can be estimated from the hypnogram:
delay in sleep onset;
lower sleep efficacy (<90%); and
numerous sleep stage shifts (NREM sleep stages N3, N2, and N1).

A general form for the index Ip is shown in Equation 1, below. The "t" parameter indicates time dependency, indicating that the index can be calculated over the period of an entire sleep session or a portion thereof, although this is desirably but optionally a full sleep cycle. The time dependency also enables temporal tracking of the index to, for instance, evaluate the effectiveness of a pain treatment.

$$Ip(t)=a_0+a_1\times EEG\alpha/\delta(t)+a_2\times HRV\text{-}1(t)+a_3\times Fhyp(t), \quad \text{Equation 1}$$

where $a_j=0, \ldots, 3$ are positive real numbers, $EEG\alpha/\delta$ is the spectral ratio of alpha (8-12 Hz) power to delta (0.5-4 Hz) power during deep sleep, HRV is an index of heart-rate variability (e.g. SDNN, PNN50, or HF/LF, F. Shaffer and J. P. Ginsberg, "An Overview of Heart Rate Variability Metrics and Norms," Front. Public Heal., vol. 5, no. September, pp. 1-17, 2017) calculated over a relatively short window (e.g. 30 seconds), and Fhyp is an index estimated from the hypnogram that characterizes specific effects of pain in sleep architecture.

Equation 2 defines Fhyp as a linear combination of sleep latency (SL), i.e., the amount of time it takes to go from being fully awake to sleeping, sleep efficiency (SE), i.e., the ratio of time asleep to time in bed, and an average duration of a number of N3 or other sleep bouts.

$$Fhyp(t)=b_0+b_1\times SL(t)+b_2\times SE(t)+b_3\times N3bout(t), \quad \text{Equation 2}$$

where $b_j=0, \ldots, 3$ are positive real numbers.

The values of the coefficients $a_j=0, \ldots, 3$ and $b_j=0, \ldots, 3$ can be personalized by using statistical methods (such as regression models) along with patient annotated data for pain levels.

Figure 2A:
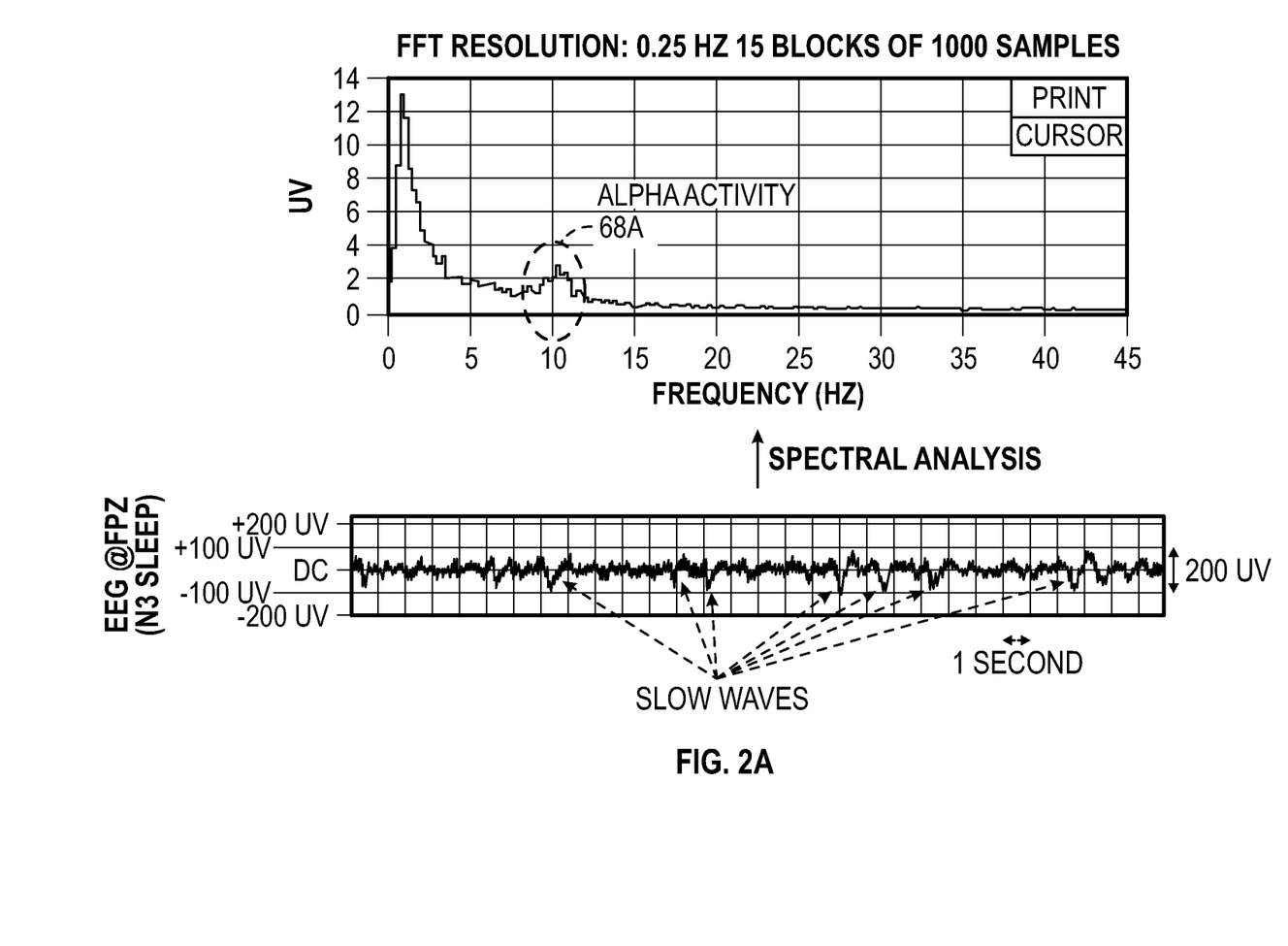
FIGS. 2A and 2B are spectral analysis, with FIG. 2A showing alpha intrusion in deep sleep, wherein deep sleep slow-waves are visible in the EEG along with superposed oscillations in the alpha (8-14 Hz) band, and which is confirmed by the spectral analysis, and with FIG. 2B showing an example of a deep sleep EEG signal without alpha intrusion.
Figure 2B:
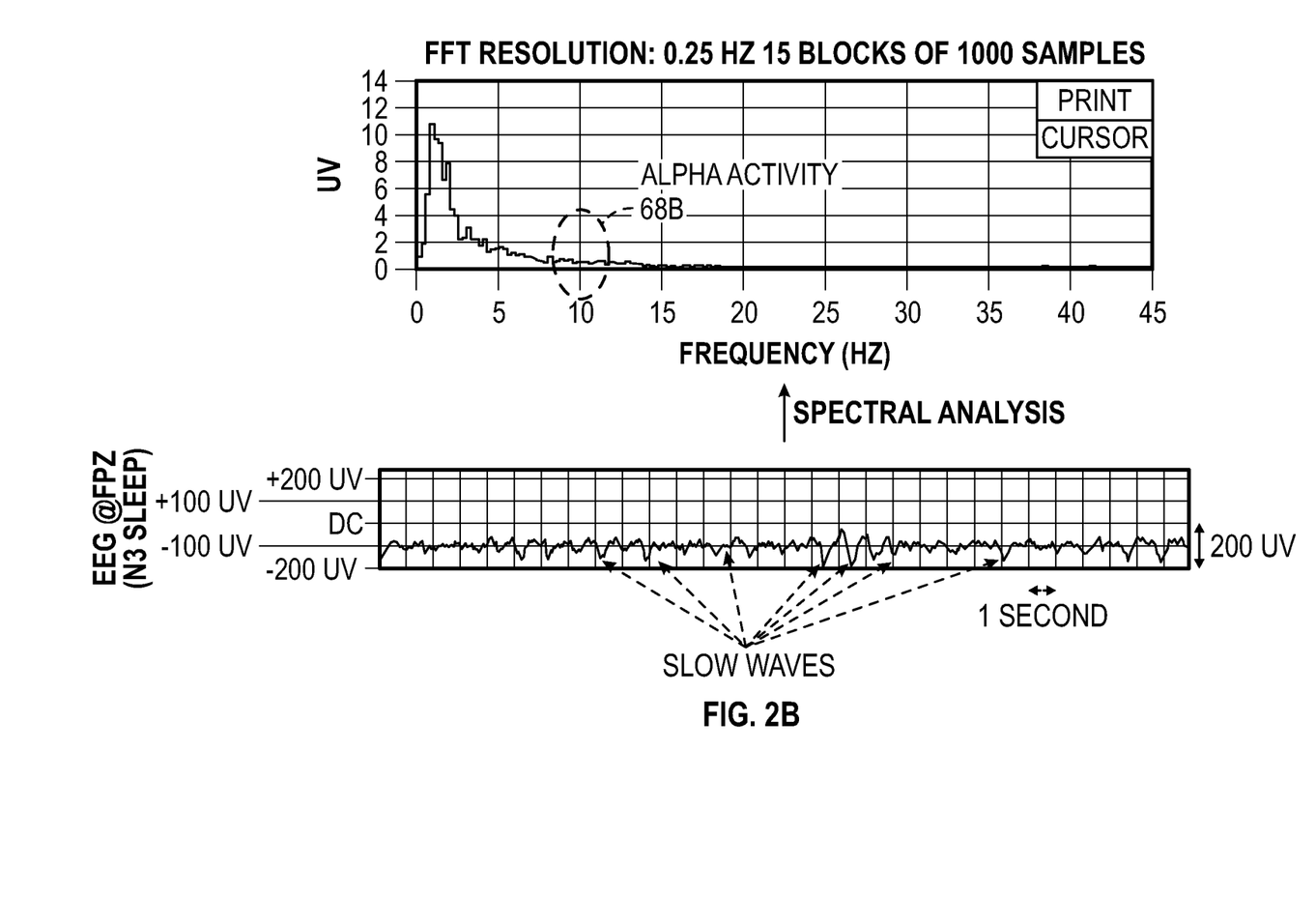
Figure 3:
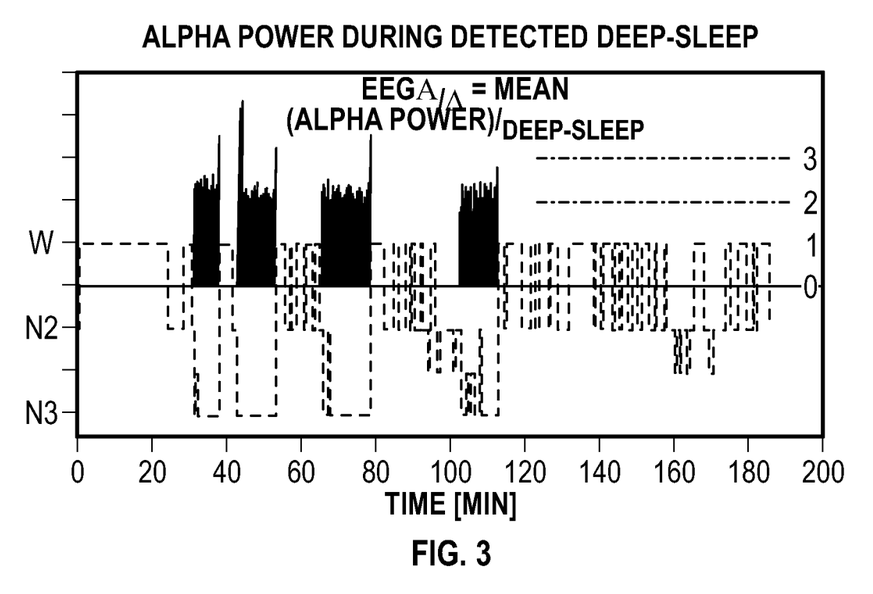
FIG. 3 is a depiction of a hypnogram that is a quantification of the index of alpha intrusion in deep-sleep.

EEG-Based Detection of Alpha Intrusion in Slow-Wave Sleep:

Alpha intrusion (alpha/delta pattern) in deep sleep is a marker of non-restorative sleep due to chronic pain (R. M. Wittig, F. J. Zorick, D. Blumer, M. Heilbronn, and T. Roth, "Disturbed sleep in patients complaining of chronic pain," J.Nerv.Ment.Dis., vol. 170, no. 7. pp. 429-31, 1982) and can be observed in the EEG, as is shown in FIG. 2A at the numeral 68A. The index of alpha intrusion in deep sleep "$EEG\alpha/\delta(t)$" (see Equation 1) can be calculated using the average alpha power during detected deep sleep. Automatic detection of deep sleep in the EEG can accomplished with a consumer device, an example of which is the Philips SmartSleep deep sleep headband, although other devices can be employed. G. Garcia-Molina et al., "Hybrid in-phase and continuous auditory stimulation significantly enhances slow wave activity during sleep," 2019 41st Annual International Conference of the IEEE Engineering in Medicine and Biology Society (EMBC), 2019, pp. 4052-55; G. Garcia-Molina et al., "Closed-loop system to enhance slow-wave activity," J. Neural Eng., vol. 15, no. 6, pp. 1-11, 2018; E. Bresch, U. Grossekathofer, and G. Garcia-Molina, "Recurrent deep neural networks for real-time sleep stage classification from single channel EEG," Front. Comput. Neurosci., vol. 12, no. 2018, pp. 1-12, 2018. The illustration of the method can be observed in FIG. 3.

HRV Metrics in Slow-Wave Sleep:

In the disclosed and claimed concept, heart rate variability (HRV) is estimated during detected slow-wave sleep. HRV is the measure of variability in the time intervals between adjacent heartbeats, RR intervals, within a pre-defined temporal window. In the disclosed and claimed concept the window duration is relatively short≤30 seconds, by way of example. Typically, HRV calculations are performed on NN intervals, i.e., RR intervals from which artifacts have been removed. Rajendra Acharya, U., Paul Joseph, K., Kannathal, N., et al. "Heart rate variability: a review," Med. Bio. Eng. Comput. 44, 1031-51 (2006); https://doi.org/10.1007/s11517-006-0119-0.

Slow-wave sleep is directly detected using cardiac signals (P. Fonseca et al., "Validation of Photoplethysmography-Based Sleep Staging Compared With Polysomnography in Healthy Middle Aged Adults," Sleep, vol. 3, 2017) using relatively longer temporal windows (i.e., >30 seconds). In some embodiments, cardiac signals and EEG signals are simultaneously detected and recorded, and in such a situation the EEG signal can be used for detection of slow-wave sleep. "Hybrid in-phase and continuous auditory stimulation significantly enhances slow wave activity during sleep", supra; "Closed-loop system to enhance slow-wave activity", supra; "Recurrent deep neural networks for real-time sleep stage classification from single channel EEG", supra.

Time-domain indices of HRV directly quantify NN. Frequency-domain measurements estimate the distribution of absolute or relative power of the NN intervals into four frequency bands: ultra-low frequency (ULF≤0.003 Hz), very-low frequency (VLF; 0.0033-0.04 Hz), low frequency (LF; 0.04-0.15 Hz) and high frequency (HF; 0.15-0.40 Hz). "An Overview of Heart Rate Variability Metrics and Norms", supra. In the disclosed and claimed concept, which uses a short time window, the HRV metric considered is HF/LF.

Hypnogram-Based Sleep Disturbance Calculation:

The index of sleep architecture (hypnogram) disturbance is calculated using the general formulation in Equation 2. In the preferred embodiment, $b_0=0$; $b_1=1$; $b_2=1$; and $b_3=1$.

Estimation of Index of Sleep Disturbance Due to Pain:

The analytical description of the index is presented in Equation 1. In the preferred embodiment the coefficients $a_j=0, \ldots, 3$ are estimated using annotated data for which pain level and predictor values $EEG\alpha/\delta$, HRV-1, and, Fhyp are known. However, in some embodiments it is envisioned to start with the initial values $a_0=0$; $a_1=1/3$; $a_2=1/3$; $a_3=1/3$ and iteratively adjust them depending on the patient experience of pain. Furthermore, it is noted that these coefficients, as well as the $b_j$ coefficients, and the index of pain itself, as well as the index of sleep disturbance, can all be adjusted based on real time data, such as with the use of a closed loop system.

In other embodiments, some of the elements listed in Equation 1 may not be available due to limited monitoring, such as if, for instance, only cardiac signals are recorded and without an EEG. The index can still be calculated but the coefficient associated with the missing signal is set to 0.

Extensions to Reduced States of Consciousness:

In post-coma unresponsiveness states or during anesthetic sedation, patterns of brain and autonomic activity similar to that in deep sleep have been reported. R. D. Sanders, G. Tononi, S. Laureys, and J. W. Sleigh, "Unresponsiveness versus unconsciousness," Anesthesiology, vol. 116, no. 4, pp. 946-59, Nov. 2012. Thus, the index proposed in this invention advantageously can also inform on pain experience during those states. As such, and as used herein, the expression "reduced consciousness" shall refer broadly to any one or more states of an individual that can include vegetative states, anesthetic sedation, and sleep.

Extensions to Acute Pain:

The index proposed in the disclosed and claimed concept advantageously can be used as an indicator of sleep disturbance due to acute pain. This is particularly useful for patients with cognitive challenges or those with communication difficulties. This can further be extended to any of a number of non-communicative patients or patients with limited communications, such as ALS patients, children, those with language challenges, those with battlefield injuries, and the like, by way of example. For instance, the application of the improved apparatus and/or method set forth herein to non-communicative patients or patients with limited communications is highly advantageous inasmuch as the improved apparatus and method do not rely for their efficacy upon communications from a patient, and rather are based upon data and signals obtained from a patient.

Applications:

Signals to calculate Ip could be drawn from a variety of sources such as therapy devices, upgraded Bispectral (BIS) devices for depth-of-anesthesia monitoring, and/or consumer-oriented devices such as the SmartSleep deep-sleep headband, as well as similar devices. Alternately, purpose-designed devices might be developed to optimize the efficient collection of these signals.

Chronic and Acute Pain Suffering Individuals:

The index Ip can be used to calculate and/or otherwise determine periodic adjustments to interventions for individuals suffering from pain. If the intervention is pharmaceutical, the dose level and timing of medicines can be tuned based on Ip to a level with situational awareness of the individual's immediate overall condition. With pain medication advantageously tuned in this way, acute pain would be ameliorated, while lesser pains would not be overmedicated. This solution would provide an objective measure of the pain experienced by an individual. This can furthermore have a beneficial impact upon opioid and related crises such as those involving addition and abuse scenarios.

Special-Case Use, Individuals Lacking Ability to Communicate Pain to Caregivers:

There exist numerous scenarios where an individual suffering pain is unable to communicate with their caregiver. Some scenarios include disease related (ALS, stroke, etc.), others relate to injury (battlefield, accidents), others relate to medical-related conditions (coma, anesthesia, etc.), others relate to the challenges of foreign-languages, and still other examples include infants and pre-speech children. In these special cases, the solution described above would be particularly valuable to help tune treatment plans to the individual and immediate situation.

Figure 4:
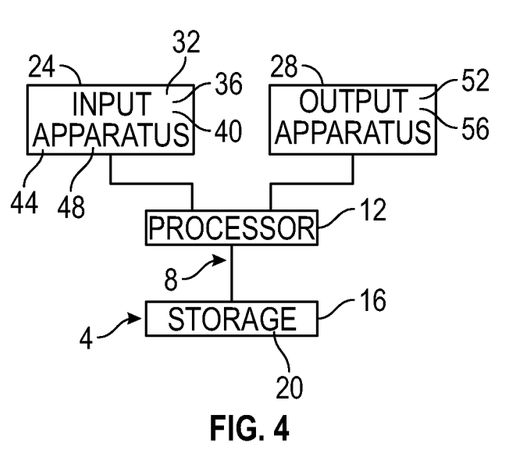
FIG. 4 depicts an apparatus in accordance with the disclosed and claimed concept.

An improved apparatus 4 in accordance with the disclosed and claimed concept is depicted in a schematic fashion in FIG. 4. Apparatus 4 can be employed in performing an improved method 100 that is likewise in accordance with the disclosed and claimed concept and at least a portion of which is depicted in a schematic fashion in FIG. 5. Apparatus 4 can be characterized as including a processor apparatus 8 that can be said to include a processor 12 and a storage 16 that are connected with one another. Storage 16 is in the form of a non-transitory storage medium has stored therein a number of routines 20 that are likewise in the form of a non-transitory storage medium and that include instructions which, when executed on processor 12, cause apparatus 4 to perform certain operations such as are mentioned elsewhere herein.

Apparatus 4 can be said to further include an input apparatus 24 that provides input signals to processor 12 and an output apparatus 28 that receives output signals from processor 12. Input apparatus 24 can be said to include any of a variety of input components, and output apparatus 28 can likewise be said to include any of a variety of output components. For instance, if apparatus 4 includes a touchscreen, output apparatus 28 might be said to include a visual display of the touchscreen, and input apparatus 24 might be said to include a touch-sensitive overlay that is situated atop the visual display.

Input apparatus 24 can be said to include a wide variety of monitoring devices such as, by way of example and without limitation, an EEG monitoring device 32, an ECG monitoring device 36, a PPG monitoring device 40, an EMG monitoring device 44, and an EOG monitoring device 48, each of which provides signals that are representative of sleep architecture information and that are input by input apparatus 24 as input signals to processor 12.

Output apparatus 28 includes a number of output devices that include a visual display 52 and a control actuator 56. Visual display 52 can visually depict the subject matter of, for instance, FIGS. 1-3 in order to enable the signals from which the pain index is derived to be visually output. Alternatively or additionally, visual display 52 can depict the pain index itself, such as in the form of a numeric value, whether or not in the form of a graph as a function of time, or as other type of value that may include color, etc., by way of example.

Control actuator 56 is usable in any of a wide variety of fashions, such as to provide to the individual a pharmacological pain treatment or to provide pain treatment that is neurostimulation-based, behavioral-based, physiotherapy-based, etc. In this regard, it can be understood that control actuator 56 and input apparatus 24, in conjunction with processor apparatus 8 and the routines 20, can form a closed-loop control system that adapts a pain treatment regimen that is applied to the individual based upon a corresponding change in the pain index. For instance, FIG. 1 depicts at the numeral 60 the pain index of an unsuccessful pain treatment which is deemed to be unsuccessful inasmuch as the depicted pain index 60 does not meaningfully decrease over time. By way of example, such pain is evidenced in FIG. 2A at the numeral 68A, which depicts alpha intrusion in a spectral analysis of an EEG wave. In response, control actuator 56 can increase or otherwise adjust the pain treatment, such as by increasing the dosage of a drug if the pain treatment is pharmacological-based, by way of example. Other examples of a change in pain treatment would include raising the maximum limit of a self-administered pain medication, such as when a morphine button is provided to a patient in a hospital setting, wherein the patient can self-dose, but only up to a limit set by a clinician. Still other examples of adjustments to a pain treatment program can include adjustments to physical therapy and occupational therapy, such as can be instructed by the system or can be suggested to a clinician, such as through an output from the system.

To continue the example, once the dosage of the drug has reached an appropriate level, the pain index that is output, as in FIG. 1 at the numeral 64, will decrease over time to an acceptable pain level. It thus can be understood that pain index 64 depicts a successful treatment of pain in the individual. This is also depicted, by way of example, with the absence of alpha intrusions, as at the numeral 68B in FIG. 2B in the spectral analysis of the EEG signal. Other variations will be apparent depending upon the pain treatment regimen, the input signals representative of sleep architecture that are being employed, and the like, by way of example.

Figure 5:
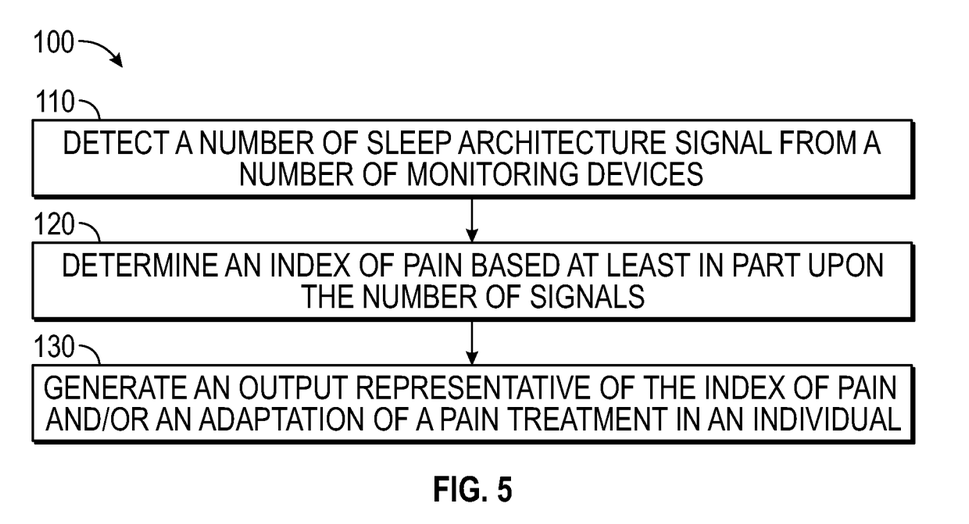
FIG. 5 depicts an improved method in accordance with the disclosed and claimed concept.

An improved method 100 in accordance with the disclosed and claimed concept is depicted generally in FIG. 5. Processing begins, as at 110 with, during at least a portion a period of reduced consciousness of an individual, detecting (110) a number of signals from a number of monitoring devices applied to the individual. As noted herein, the number of monitoring devices can include any one or more of an EEG 32, an ECG 36, a PPG 40, an EMG 44, and an EOG 48, by way of example.

Processing continues, as at 120, with the determining of an index of pain in the individual based at least in part upon the number of signals. The index of pain can be determined, for instance, from Equation 1 and, optionally, with the additional use of Equation 2 if a hypnogram is being employed.

Processing continues, as at 130, with the generating of an output that is representative at least in part of at least one of i) the index of pain, and ii) an adaptation of a pain treatment of the individual. As noted hereinbefore, the index of pain can be employed to perform the adaptation of the pain treatment. Such an output can be employed in conjunction with continuously fine tuning the index of pain over time.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of optimization of a pain treatment in an individual, comprising:
    during at least a portion a period of reduced consciousness of the individual, detecting a number of signals from a number of monitoring devices applied to the individual, wherein the detecting of the number of signals comprises receiving a cardiac input based at least in part upon at least one of an ECG signal from an ECG monitoring device and a PPG signal from a PPG monitoring device;
    determining an index of pain in the individual based at least in part upon the number of signals, wherein the index of pain is based at least in part on: (i) a spectral ratio of alpha power to delta power during that at least a portion of the period of reduced consciousness, (ii) an index of heart-rate variability (HRV) obtained at least in part from the cardiac input, and (iii) an index comprising a linear combination of sleep latency (SL), a sleep efficiency (SE), and an average duration of a number of sleep bouts; and
    causing a control actuator to
    a pain treatment of the individual based at least in part on the index of pain.

2. The method of claim 1 wherein the detecting of the number of signals comprises detecting one or more of an electroencephalogram (EEG) signal from an EEG monitoring device, an electrocardiogram (ECG) signal from and ECG monitoring device, a photoplethysmogram (PPG) signal from a PPG monitoring device, an electromyogram (EMG) signal from an EMG monitoring device, and an electrooculogram (EOG) signal from an EOG monitoring device.

3. The method of claim 1 wherein the detecting of the number of signals comprises detecting an EEG signal from an EEG monitoring device, and further comprising detecting an alpha intrusion during that at least portion of the period of reduced consciousness, the index of pain being based at least in part upon the alpha intrusion.

4. The method of claim 1 wherein the control actuator is structured and configured to control a pharmacologically-based pain treatment of the individual, wherein the causing the control actuator to adapt the pain treatment comprises adapting a dosage of the pharmacologically-based pain treatment depending on at least the index of pain.

5. The method of claim 1 wherein the causing the control actuator to adapt the pain treatment comprises adapting at least one of a neurostimulation-based pain treatment of the individual, a behavioral-based pain treatment of the individual, and a physiotherapy-based pain treatment of the individual.

6. An apparatus structured to optimize a pain treatment in an individual, comprising:
    a processor apparatus comprising a processor and a storage;
    an input apparatus structured to provide a number of input signals to the processor apparatus;
    an output apparatus structured to receive a number of output signals from the processor apparatus;
    a control actuator; and
    the storage having stored therein a number of instructions which, when executed on the processor, cause the apparatus to perform a number of operations comprising:
    during at least a portion a period of reduced consciousness of the individual, detecting a number of signals from a number of monitoring devices applied to the individual, wherein the detecting of the number of signals comprises receiving a cardiac input based at least in part upon at least one of an ECG signal from an ECG monitoring device and a PPG signal from a PPG monitoring device;
    determining an index of pain in the individual based at least in part upon the number of signals, wherein the index of pain is based at least in part on: (i) a spectral ratio of alpha power to delta power during that at least a portion of the period of reduced consciousness, (ii) an index of heart-rate variability (HRV) obtained at least in part from the cardiac input, and (iii) an index comprising a linear combination of sleep latency (SL), a sleep efficiency (SE), and an average duration of a number of sleep bouts; and causing the control actuator to a pain treatment of the individual based at least in part on the index of pain.

7. The apparatus of claim 6 wherein the detecting of the number of signals comprises detecting one or more of an electroencephalogram (EEG) signal from an EEG monitoring device, an electrocardiogram (ECG) signal from and ECG monitoring device, a photoplethysmogram (PPG) signal from a PPG monitoring device, an electromyogram (EMG) signal from an EMG monitoring device, and an electrooculogram (EOG) signal from an EOG monitoring device.

8. The apparatus of claim 6 wherein the detecting of the number of signals comprises detecting an EEG signal from an EEG monitoring device, and wherein the operations further comprise detecting an alpha intrusion during that at least portion of the period of reduced consciousness, the index of pain being based at least in part upon the alpha intrusion.

9. The apparatus of claim 6 wherein the control actuator is structured and configured to control a pharmacologically-based pain treatment of the individual, wherein the causing the control actuator to adapt the pain treatment comprises adapting a dosage of the pharmacologically-based pain treatment depending on at least the index of pain.

10. The apparatus of claim 6 wherein the causing the control actuator to adapt the pain treatment comprises adapting at least one of a neurostimulation-based pain treatment of the individual, a behavioral-based pain treatment of the individual, and a physiotherapy-based pain treatment of the individual.

* * * * *